United States Patent [19]

Chance

[11] Patent Number: 5,402,778

[45] Date of Patent: Apr. 4, 1995

[54] SPECTROPHOTOMETRIC EXAMINATION OF TISSUE OF SMALL DIMENSION

[75] Inventor: Britton Chance, Marathon, Fla.

[73] Assignee: NIM Incorporated, Philadelphia, Pa.

[21] Appl. No.: 6,233

[22] Filed: Jan. 19, 1993

[51] Int. Cl.$^6$ .............................................. A61B 5/00
[52] U.S. Cl. .................................. 128/633; 128/664; 128/665; 356/39
[58] Field of Search ................... 128/633.4, 637, 664, 128/665–667; 356/39–41

[56] References Cited

U.S. PATENT DOCUMENTS

| | | | |
|---|---|---|---|
| 3,461,856 | 8/1969 | Polanyi | 356/41 |
| 3,638,640 | 2/1972 | Shaw | |
| 3,994,585 | 11/1976 | Frey | 356/40 |
| 3,998,550 | 12/1976 | Konishi et al. | 356/39 |
| 4,086,915 | 5/1978 | Kofsky et al. | |
| 4,138,727 | 2/1979 | Mantz | 364/525 |
| 4,167,331 | 9/1979 | Nielsen | 356/40 X |
| 4,223,680 | 9/1980 | Jöbsis | 128/633 |
| 4,281,645 | 8/1981 | Jöbsis | 128/633 |
| 4,321,930 | 3/1982 | Jöbsis | 128/633 |
| 4,380,240 | 4/1983 | Jöbsis | 128/633 |
| 4,510,938 | 4/1985 | Jöbsis et al. | 128/633 |
| 4,714,341 | 12/1987 | Hamaguri et al. | 356/41 |
| 4,800,495 | 1/1989 | Smith | 364/413.03 |
| 4,800,885 | 1/1989 | Johnson | 128/633 |
| 4,824,242 | 4/1989 | Frick et al. | 356/41 |
| 4,846,183 | 4/1989 | Martin | 128/633 |
| 4,908,762 | 3/1990 | Suzuki et al. | 364/413.09 |
| 4,972,331 | 11/1990 | Chance | 364/550 |
| 5,119,815 | 6/1992 | Chance | 128/633 |
| 5,187,672 | 2/1993 | Chance et al. | 364/550 |

OTHER PUBLICATIONS

Chance, B., Nioka, S., Kent, J., McCully, K., Gountain, M., Greenfeld, R. and Holtom, G. "Time Resolved Spectroscopy of Hemoglobin and Myoglobin Resting and Ischemic Muscle," *Anal. Biochem.* 174:698–707 (1988).

Chance, B., Smith, D. S., Nioka, S., Miyake, H., Holtom, G. and Maris, M. pp. 121–135 "Photon Migration in Muscle and Brain," *Photon Migration in Tissues*, Plenum Press (1989), Chance, B., ed.

Bonner, R. F., Nossal, R., Havlin, S., and Weiss, G. H., "Model for photon migration in turbid biological media", *J. Opt. Soc. Am. A.* vol. 4, No. 3, pp. 423–427 (Mar. 1987).

Chance et al., "Comparison of time-resolved and -unresolved measurements of deoxyhemoglobin in brain," *Proc. Natl. Acad. Sci* vol. 85, pp. 4971–4975, Jul. 1988.

(List continued on next page.)

Primary Examiner—Angela D. Sykes
Attorney, Agent, or Firm—Fish & Richardson

[57] ABSTRACT

A system for examination of a relatively small volume of biological tissue of interest using visible or infra-red radiation includes a spectrophotometer, an optical medium of a relatively large volume having selectable scattering and absorptive properties, and a processor adapted to determine a physiological property of the examined tissue. The spectrophotometer includes a light source for introducing radiation at an optical input port, a detector for detecting radiation that has migrated through a path from the input port to an optical detection port, and a processor for evaluating changes between the introduced and the detected radiation. The biological tissue of interest is positioned into the photon migration path inside the optical medium to create a tissue-medium optical path. The optical medium is adapted to limit substantially escape of photons from the tissue. The processor determines a physiological property of the tissue based on the detected optical property of the tissue-medium optical path and the scattering or absorptive properties of the selected optical medium. Alternatively, the system can match the optical properties of the medium to the optical properties of the tissue. The spectrophotometer is a continuous wave spectrophotometer, a phase modulation spectrophotometer or a time-resolved spectrophotometer.

33 Claims, 12 Drawing Sheets

OTHER PUBLICATIONS

Greenfield, "A Tissue Model For Investigating Photon Migration in Trans-Cranial Infrared Imaging," *Photon Migration in Tissues*, pp. 147–168, 1988.

Fishkin, "Diffusion of Intensity Modulated Near-Infrared Light In Turbin Media," *SPIE*, vol. 1431, pp. 122–135, 1991.

Oda et al., "Non-invasive hemoglobin oxygenation monitor and computed tomography by NIR spectrophotometry," pp. 284–293, *SPIE*, vol. 1431, 1991.

Sevick et al., "Analysis of absorption, scattering, and hemoglobin saturation using phase modulation spectroscopy," *SPIE* vol. 1431, pp. 264–275, 1991.

Sevick et al., "Photon migration in a model of the head measured using time –and frequency– domain techniques: potentials of spectroscopy and imaging," *SPIE*, vol. 1431, pp. 84–96, 1991.

Cui et al., "Experimental Study of Migration Depth for the Photons Measured at Sample Surface," *SPIE*, vol. 1431, pp. 180–191, 1991.

Weng et al., "Measurement of Biological Tissue Metabolism Using Phase Modulation Spectroscopy Technology," *SPIE*, vol. 1431, Time-Resolved Spectroscopy and Imaging of Tissue (1991).

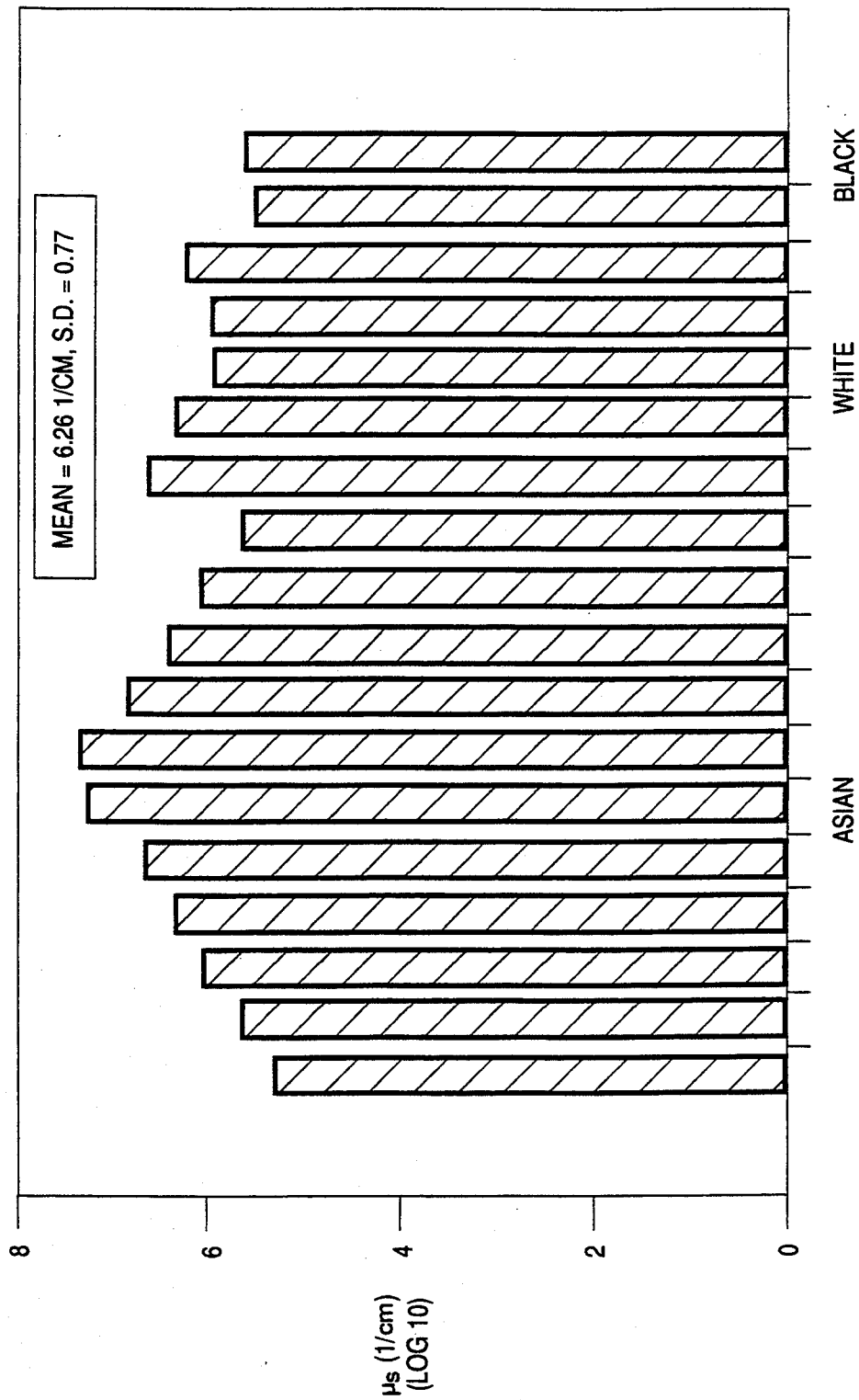

SPECTROPHOTOMETRIC EXAMINATION OF TISSUE OF SMALL DIMENSION

CROSS REFERENCE TO RELATED APPLICATIONS

The present invention is related to U.S. patent application Ser. No. 07/876,364, filed Apr. 30, 1992, now abandoned, which is a continuation application of U.S. Pat. No. 5,119,815, issued Jun. 9, 1992 and is also related to U.S. patent application Ser. No. 645,590 filed Jan. 24, 1991, now abandoned, U.S. patent application Ser. No. 644,090 filed Jan. 22, 1991, now U.S. Pat. No. 5,187,672, and U.S. patent application Ser. No. 701,127, filed May 16, 1991, now abandoned, all of which are incorporated by reference as if set forth in their entities herein.

BACKGROUND OF THE INVENTION

Continuous wave (CW) spectrophotometers have been widely used to determine in vivo concentration of an optically absorbing pigment (e.g., hemoglobin, oxyhemoglobin) in biological tissue. The CW spectrophotometers, for example, in pulse oximetry introduce light into a finger or the ear lobe to measure the light attenuation and then evaluate the concentration based on the Beer Lambert equation or modified Beer Lambert absorbance equation. The Beer Lambert equation (1) describes the relationship between the concentration of an absorbent constituent (C), the extinction coefficient ($\epsilon$), the photon migration pathlength $<L>$, and the attenuated light intensity ($I/I_o$).

$$\frac{\log[I/I_0]}{<L>} = \Sigma \, \epsilon_i C_i \qquad (1)$$

However, direct application of the Beer Lambert equation poses several problems. Since the tissue structure and physiology vary significantly, the optical pathlength of migrating photons also varies significantly and can not be simply determined from geometrical position of a source and detector. In addition, the photon migration pathlength itself is a function of the relative concentration of absorbing constituents. As a result, the pathlength through an organ with high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. One solution to this problem is to determine $\epsilon$, C, and $<L>$ at the same time, but this is not possible with the CW oximeters.

Furthermore, for quantitative measurement of tissue of a small volume (e.g., a finger) photon escape introduces a significant error since the photons escaped from the tissue are counted as absorbed.

There are several reasons for using in vivo tissue oximetry. Although the arterial oxygen saturation can be in vitro quantified, it is not possible to estimate the change in the hemoglobin oxygen concentration as it leaves an artery and enters the capillary bed. Neither is it possible to determine the intermediate value of oxygen saturation in a particular capillary bed from the venous drainage since no technique has been devised for drawing a blood sample directly from the capillary bed. In the time resolved (TRS-pulse) and phase modulation (PMS) spectrophotometers that can measure the average pathlength of migrating photons directly, but the proper quantitation of the time resolved or frequency resolved spectra can be performed only when the spectra are collected at a relatively large source-detector separation. This separation is difficult to achieve for a small volume of tissue such as the earlobe, a finger or a biopsy tissue.

Therefore, there is a need for a spectrophotometric system and method for quantitative examination of a relatively small volume of biological tissue.

SUMMARY OF THE INVENTION

The invention features a spectrophotometric system for examination of a relatively small volume of biological tissue of interest using visible or infra-red radiation.

According to one aspect of the invention, a spectrophotometric system for examination of a relatively small object of interest (e.g., biological tissue, organic or inorganic substance in a solid, liquid or gaseous state) using visible or infra-red radiation introduced to a path passing through the object. The system includes a spectrophotometer with an optical input port adapted to introduce radiation into the object and an optical detection port adapted to detect radiation that has migrated through a path in the object, photon escape preventing means arranged around the relatively small object of interest and adapted to limit escape of the introduced photons outside the object, and processing means adapted to determine an optical property of the object based on the changes between the introduced and the detected radiation.

According to another aspect of the invention, a system for examination of a relatively small volume of biological tissue of interest using visible or infra-red radiation includes a spectrophotometer with a light source adapted to introduce radiation at an optical input port, a detector adapted to detect radiation that has migrated through a path from the input port to an optical detection port, and a processor adapted to evaluate changes between the introduced and the detected radiation. The system also includes an optical medium of a relatively large volume, forming photon preventing means, having selectable scattering and absorptive properties, positioning means adapted to locate the biological tissue of interest into the migration path to create a tissue-medium optical path, the optical medium substantially limiting escape of photons from the tissue-medium optical path, and processing means adapted to determine a physiological property of the tissue based on the detected optical property of the tissue-medium optical path and the scattering or absorptive properties of the optical medium.

Preferred embodiments of these aspects of the invention include one or more of the following features.

The photon escape preventing means include an optical medium of a selectable optical property surrounding the object. The selectable optical property is an absorption or scattering coefficient.

The photon escape preventing means include an optical medium surrounding the object; the medium has at least one optical property substantially matched to the optical property of the object.

The spectrophotometer is a continuous wave spectrophotometer, a phase modulation spectroscopic unit or time resolved spectroscopic unit.

The determined physiological property is the hemoglobin saturation, the concentration of an enzyme or the concentration of a tissue substance such as glucose.

The system performs a single measurement or a continuous, time-dependent monitoring of the selected physiological property.

The above-described system operates by introducing into the object, surrounded by the photon escape preventing means, electromagnetic radiation of a selected wavelength and detecting radiation that has migrated in the object from the input port to the optical detection port. The system determines an optical property of the object based on the changes between the introduced and the detected radiation. In addition, different photon escape preventing means having a surrounding optical medium with the optical property comparable to the optical property of the object may be selected. Then, the system measures again the optical property of the object. The measurements may be repeated iteratively until the optical property of the surrounding medium is substantially matched to the optical property of the object.

DESCRIPTION OF THE PREFERRED EMBODIMENTS

Figure 1:
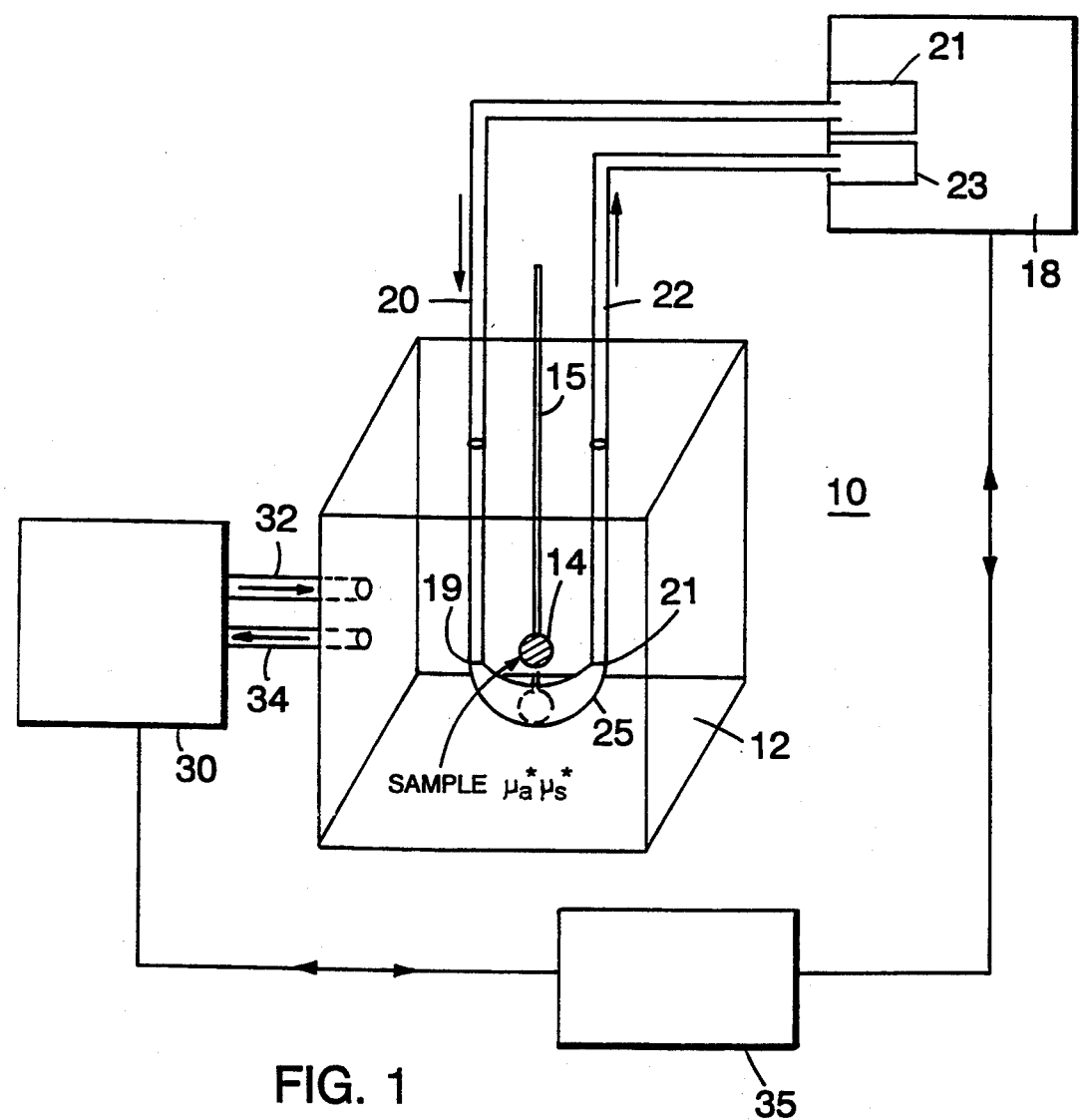
FIG. 1 is a diagrammatic view of a spectrophotometric system for examination of tissue of a relatively small dimension.

Referring to FIG. 1, a system 10 for examination of biological tissue of a relatively small volume, includes an optical medium 12 of selectable optical properties, a spectrophotometer 18, a titrimetric circulation system 30, and computer control 35. Biological tissue of interest 14, attached to a locator 15, is immersed in optical medium 12. Spectrophotometer 18 examines optical properties of medium 12 by employing visible or infrared light conducted via light guides 20 and 22. Light guides 20 and 22, which in a preferred embodiment are optical fibers, are connected to a light source 21 and a light detector 23, respectively. Photons introduced at an optical input port 19 migrate in medium 12 through a scattering and absorptive path and are detected at a detection port 21. The selectable fixed geometry of input port 19 and detection port 21 controls the migration path, i.e., optical field 25.

System 30 is adapted to change precisely the scattering and absorptive properties of medium 12. Medium 12 includes intralipid solution (made by Kabi Vitrum, Inc., Clapton, N.C.) that exhibits scattering properties depending on its concentration and carbon black india ink that exhibits absorptive properties. The scattering or absorptive properties of medium 12 can be either maintained constant and uniform by properly mixing the solution or can be changed almost continuously by changing the concentration of the constituents in titration system 30. Tubes 32 and 34 are adapted for continuous circulation of the solution.

In system operation, tissue 14 is first located away from optical field 25. Spectrophotometer 18 examines medium 12 in field region 25, and control 35 compares the detected data to the preselected values of the absorption coefficient ($\mu_a$) and the scattering coefficient ($\mu_s$). Next, locator 15 positions tissue 14 into field 25 and spectrophotometer 18 measures the optical properties of tissue 14 and medium 12. From the spectral data collected with and without tissue 14, computer control 35 determines the optical properties of tissue 14.

In another preferred method of operation, after measuring the optical properties of medium 12, the scattering and absorptive properties of medium 12 are matched by titration to the properties of tissue 14 so that, when inserted into field 25, tissue 14 does not cause perturbation of field 25. After matching the scattering and absorption coefficients of medium 12 to the coefficients of tissue 14, spectrophotometer 18 detects the same data with or without tissue 14. The known titrated values of $\mu_a^*$ and $\mu_s^*$ are equal to the $\mu_a$ and $\mu_s$ values of tissue 14. The matching process is performed by first matching $\mu_a$ and then $\mu_s$ or vice versa.

The described method is applicable to both in vivo and in vitro tissue examination. Tissue 14 may be a biopsy specimen enclosed in an optically transparent material or a portion of a human finger inserted into medium 12. The wavelength of light used by spectrophotometer 18 is selected depending on the tissue component of interest (e.g., hemoglobin, oxyhemoglobin, glucose, enzymes); it is within the scope of this invention to use multiple wavelengths.

Figure 2:
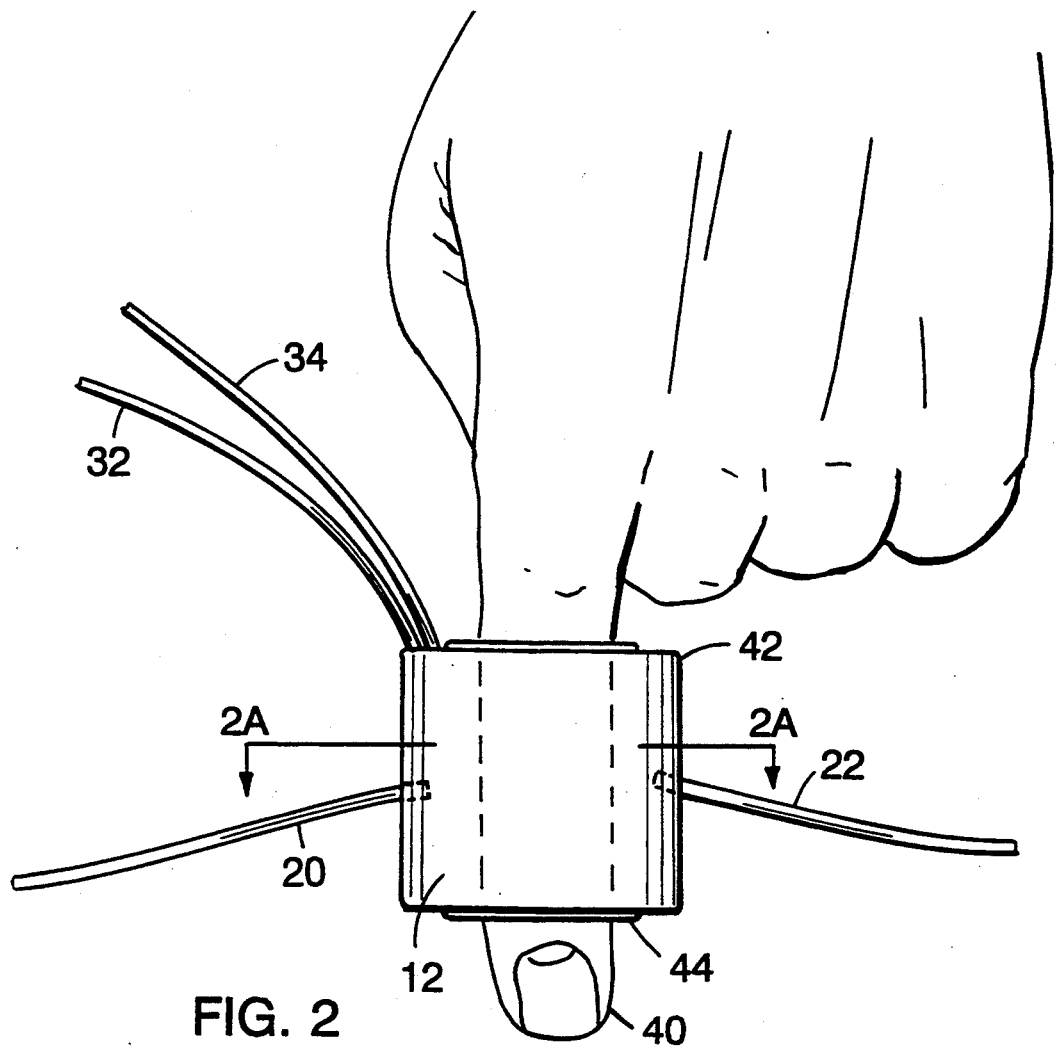
FIGS. 2 and 2A show different views of a cylinder for preventing escape of photons during spectrophotometric measurements of a finger.

The present invention envisions the use of different preferred embodiments of optical medium 12. Referring to FIG. 2, a hollow cylinder 42 filled with medium 12 surrounds, for example, a finger 40 and prevents escape of introduced photons. The optical properties, pressure and volume of medium 12 are controlled by system 30 connected to cylinder 42 by tubes 32 and 34. The inside walls of cylinder 42 are made of a pliable, optically transparent barrier 44. After insertion into cylinder 42, barrier 44 fits snugly around the finger. The dimension of inside barrier 44 is such that after finger 40 is withdrawn, medium 12 fills the volume of cylinder 42 completely. This enables both a background measurement of medium 12 and a measurement of finger 40 in medium 12 in the same way as described in connection with FIG. 1. Optical field 25, controlled by the position of input port 19 and detection port 21, is either in transmission or reflection geometry.

Figure 2A:
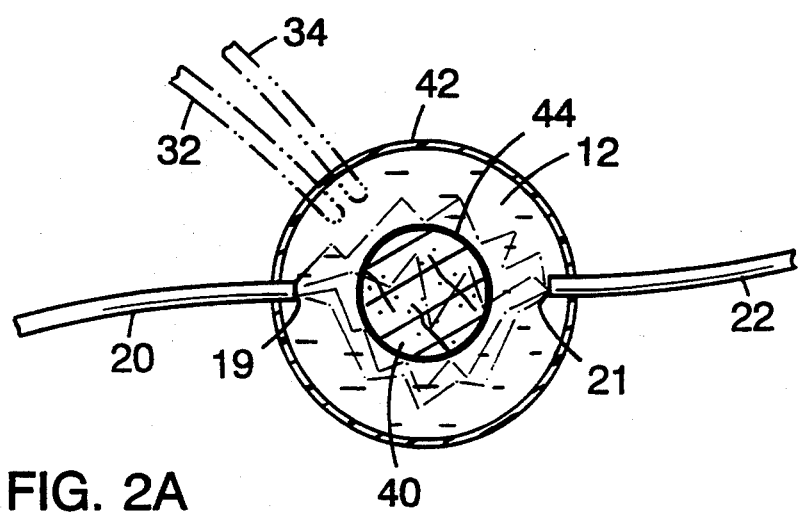
Figure 2B:
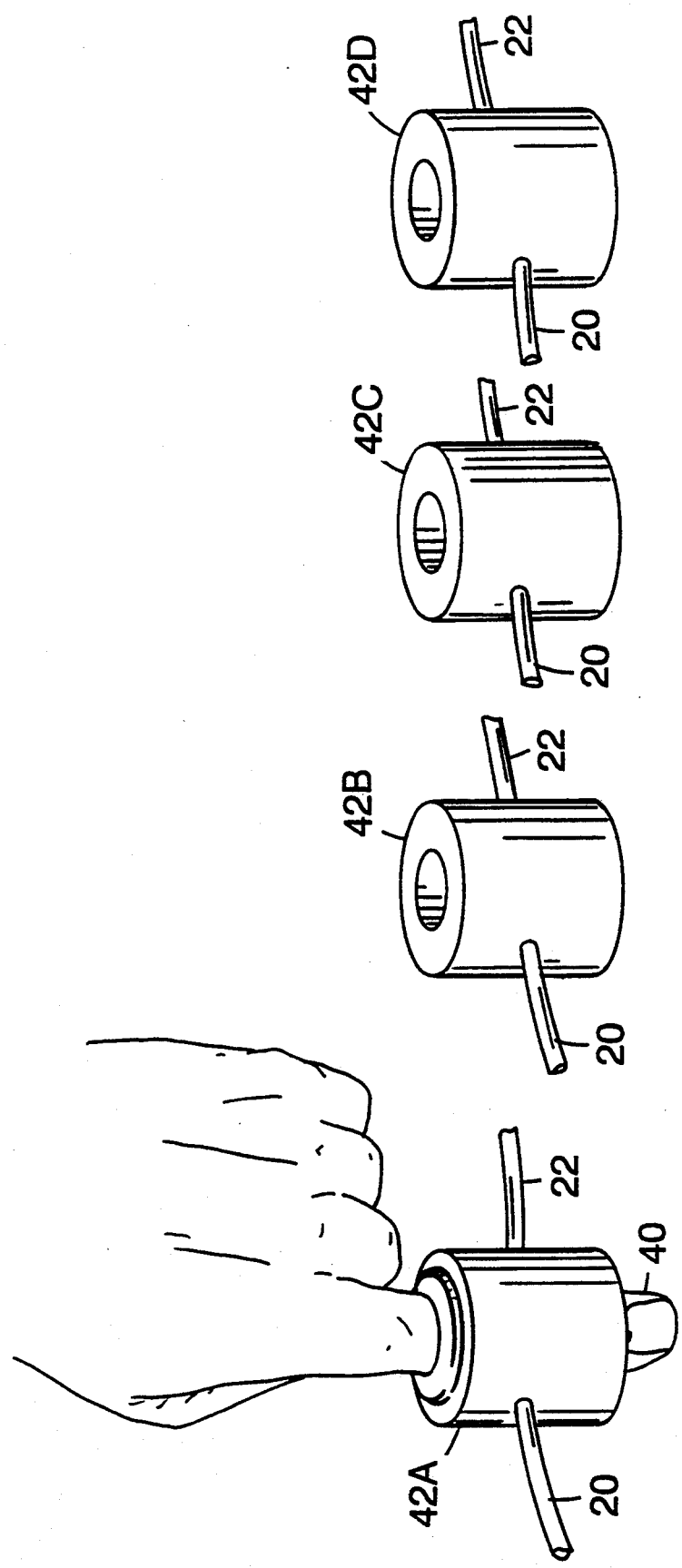
FIG. 2B shows a set of cylinders of preselected optical properties for a finger oximetry.

Referring to FIG. 2B, in another embodiment, cylinder 42 is replaced by a set of cylinders 42A, 42B, 42C . . . , each containing medium 12 in a fluid or solid state with a constant preselected absorption and scattering coefficient. The solid optical medium is titanium oxide, or other scatterer, imbedded in an absorbing, pliable medium such as a gel.

A human finger is inserted into the individual cylinders, and the optical properties of the inserted finger are measured by spectrophotometer 18. Using the known optical properties of the cylinders and the input port-detection port geometry, the optical properties (i.e., $\mu_a$ and $\mu_s$) of the finger can be matched to the properties of one of the cylinders.

The preferred embodiments of spectrophotometer 18 are a continuous wave spectrometer, a phase modulation spectrometer and a time-resolved spectrometer, all of them described in the above-cited documents.

System 10 operating with a dual wavelength continuous wave spectrometer is used, for example, as a finger oximeter. As shown in FIG. 2A, the vast majority of photons introduced into finger 40 are prevented to escape by surrounding medium 12. Thus, the introduced photons are either absorbed or reach detection port 21 and are registered by the detector. No error of counting the escaped photons as absorbed occurs. The background spectral data corresponding to each selected value of $\mu_a^*$ and $\mu_s^*$ of cylinder 42 are stored in the system that can match the values of $\mu_a$ and $\mu_s$ of the finger and the cylinder for each wavelength. For the continuous wave spectrometer that operates at two wavelengths sensitive to hemoglobin (Hb) and oxyhemoglobin (HbO$_2$) (e.g., 754 nm and 816 nm), the hemoglobin saturation (Y) is calculated by taking the ratio of absorption coefficients and using the following equation for the oxygen saturation:

$$Y(X100\%) = \frac{38 - 18 \frac{\mu_a^{754}}{\mu_a^{816}}}{25 + 3 \frac{\mu_a^{754}}{\mu_a^{816}}} \quad (2)$$

wherein the coefficients are determined from the extinction values of hemoglobin at 754 nm and 816 nm that are $\epsilon_{Hb}=0.38$ cm$^{-1}$ mM$^{-1}$, $\epsilon_{Hb}=0.18$ cm$^{-1}$ mM$^{-1}$, respectively, and the difference extinction coefficients between oxyhemoglobin and hemoglobin that are $\Delta\epsilon_{HbO-Hb}=0.025$ cm$^{-1}$ mM$^{-1}$ and $\Delta\epsilon_{HbO-Hb}=0.03$ cm$^{-1}$ mM$^{-1}$, respectively.

As known to a person skilled in the art, in the hemoglobin saturation measurement the oximeter normalizes the detected data to eliminate fluctuations due to the changing blood volume. However, the volume changes can be used to detect the pulse rate.

Alternatively, a phase modulation spectrometer is used to measure the photon migration by detecting the intensity and the phase shift $\theta$ of sinusoidally modulated light introduced at a distance of several centimeters from the detector. For tissue of a small volume, the optimal distance between the input port and the irradiation port is achieved using optical medium 12. Furthermore, medium 12 substantially eliminates the photon escape.

The detected phase shift is directly related to the mean of the distribution of photon pathlengths shown in FIG. 2A. Photon migration theory predicts that the detected photons can be represented by a three dimensional "banana-shaped" distribution pattern in the reflection geometry or a "cigar-shaped" distribution pattern in the transmission geometry. Inserting tissue 14 into the center of field 25 causes nonuniformities in the distribution of pathlengths, i.e., the banana-shaped optical field 25 is nonuniform, if the tissue absorption properties are different from the properties of medium 12. If $\mu_a$ of the tissue is smaller then that of the surrounding medium, the average pathlength $<L>$ decreases since photons with longer pathlengths are more absorbed and vice versa. Thus, tissue 14 causes changes in the pathlength and the phase shift, $\theta$.

Furthermore, the detected intensity provides a modulation index (M) that is an important measure of the absorption and scattering properties of a strongly scattering medium. The modulation index is determined as the ratio of the AC amplitude (A$^\lambda$) to the sum of the AC and DC (DC$^\lambda$) amplitude.

$$M^{\lambda 1} = \frac{A^{\lambda 1}}{A^{\lambda 1} + DC^{\lambda 1}} \quad (3)$$

As described in Sevick et al. in Analytical Biochemistry Vol. 195, pp. 330–351, 1991, incorporated by reference as if set forth herein, for low modulation frequencies (i.e., $2\pi f << \mu_a c$) the phase shift is a direct measure of the mean time of flight, $<t>$, i.e., $\theta \to 2\pi f<t>$. In a medium wherein all photons travel at a constant speed, c, the phase shift describes the effective, mean pathlength $\theta \to 2\pi f<L>/c$. Here, all pathlengths are weighted equally. The determined pathlength is used in Beer-Lambert equation for determination of the absorption properties.

As the modulation frequency increases, the shorter pathlengths become more heavily weighted. At frequencies (i.e. $2\pi f >> \mu_a c$), the phase shift is no longer a good measure of the distribution of pathlengths and is directly proportional to the absorption coefficient, $\mu_a$, and the effective scattering coefficient, $(1-g)\cdot\mu_s$ $$|\theta^\lambda| = a\rho \sqrt{(1-g)\mu_s f} \left\{ 1 - \frac{\mu_a c}{4\pi f} \right\} \quad (4)$$

Since the effective scattering coefficient is wavelength independent, ratio of the phase shifts measured at two wavelengths can be written $$\frac{\theta^{\lambda 1} - \theta_0^{\lambda 1}}{\theta^{\lambda 2} - \theta_0^{\lambda 2}} = \frac{\mu_a^{\lambda 1}}{\mu_a^{\lambda 2}} \quad (5)$$

wherein $\theta_o^\lambda$ is the phase shift at the measured wavelength arising from the scattering and background absorption. The ratio of the absorption coefficients is used, for example, for determination of the tissue saturation, Y. A dual frequency, dual wavelength phase modulation spectrometer can be used to determine the saturation by eliminating $\theta_o$. The ratio of absorption coefficients is expressed as a function of the phase shifts measured at different frequencies and wavelengths.

$$\frac{(\theta_{f1}^{\lambda 1}/\sqrt{f_1}) - (\theta_{f2}^{\lambda 1}/\sqrt{f_2})}{(\theta_{f1}^{\lambda 2}/\sqrt{f_1}) - (\theta_{f2}^{\lambda 2}/\sqrt{f_2})} = \frac{\mu_s^{\lambda 1}}{\mu_s^{\lambda 2}} \quad (6)$$

In another preferred embodiment, a time-resolved spectrometer (TRS-pulse) introduces, at input port 19, pulses of light on the order of less than a picosecond. Photons traveling through a distribution of migration pathlengths 25 are collected at the detection port 21. The intensity of detected light in the reflectance geometry, R($\rho$,t), (or the transmittance geometry T($\rho$,d,t)) was determined by solving the diffusion equation in an infinite media as a Green's function with near infinite boundary conditions. Due to the semi-infinite media condition in the reflectance geometry, the separation of the input and output ports must be on the order of several centimeters to use the following equation.

$$\frac{d}{dt} \log_e R(\rho,t) = \frac{-5}{2t} - \mu_a c + \frac{\rho^2}{4DCt} \quad (7)$$

For $t \to \infty$ the absorption coefficient $\mu_a$ is determined as $$\lim_{t \to \infty} \frac{d}{dt} \log_e R(\rho,t) = -\mu_a c \quad (8)$$

wherein $\rho$ is the separation between input and detection ports and c is speed of light in the medium. The effective scattering coefficient $(1-g) \mu_s$ is determined as $$(1-g)\mu_s = \frac{1}{\rho^2} (4\mu_a c^2 t_{max}^2 + 10 c t_{max}) - \mu_a \quad (9)$$

wherein $t_{max}$ is the delay time at which the detected reflectance time profile $(R(\rho,t) \equiv I(t))$ reaches maximum. The right hand side of Eq. 7 is the decay slope of the arrival time of the modified pulses. The absorption coefficient is quantified by evaluating the decaying slope of the detected pulse, as described in Eq. 7. The effective scattering coefficient, $(1-g) \cdot \mu_s$, is determined from Eq. 9. For the known $\mu_a$ and $\mu_s$ and the input port, output port geometry, the system has a unique time profile $I(t)$. The stored profile is compared to the time profile detected for the introduced tissue to obtain a difference profile that possesses the scattering and absorption coefficients of tissue 14. Alternatively, $\mu_a$ and $\mu_s$ of medium 12 and tissue 14 are matched by varying the scattering and absorptive properties of medium 12 so that the detected time profile is not altered by introducing tissue 14.

The TRS system can be used to calibrate a CW oximeter to quantify the measured data. To account for the difference between the geometric distance $(\rho)$ of the input port and the detection port and the pathlength $(<L>)$, some oximeters use a modified Beer-Lambert equation with a differential pathlength factor (DPF) as follows:

$$\text{absorbance} = DPF \cdot \epsilon \cdot [C] \quad (10)$$

However, the differential pathlength factor can not be precisely determined by the CW oximeters since it depends on the pathlength. The TRS determines DPF using the absorption $(\mu_a)$ and scattering $(\mu_s)$ coefficients as follows:

$$DPF = \frac{\sqrt{3}}{2} \sqrt{\frac{(1-g)\mu_s}{\mu_a}} \quad (11)$$

Figure 3:
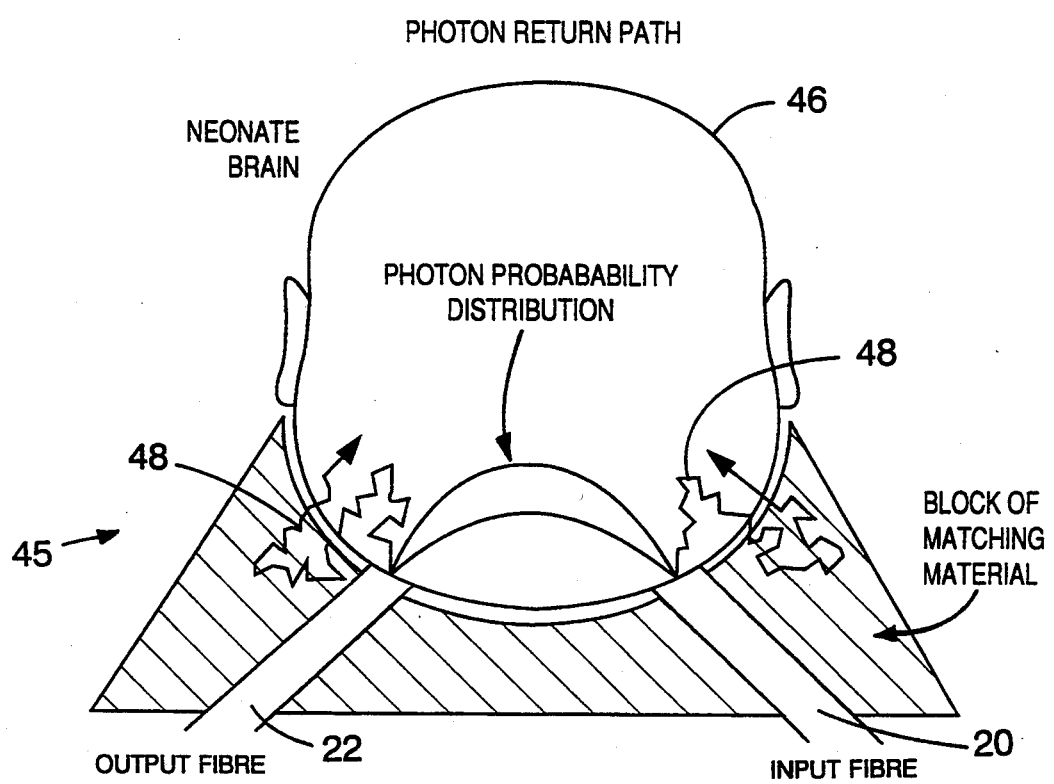
FIG. 3 is a diagrammatic view of an optical fiber holder for a spectrophotometric study of the head.

An alternative embodiment of the escape preventing optical medium used for examining the head of a neonate (46) is an optrode holder 45, shown in FIG. 3. Optical fibers 20 and 22 are projected into a solid scattering material, such as styrofoam, which affords a return pathway for escaping photons 48. The pathlength of the migrating photons in the tissue is much longer since the photons return to the tissue by the scattering materials, as shown by the zig-zag arrows 48. Thus, the banana-shaped pattern will penetrate more deeply and meaningful spectroscopic data can be obtained at smaller input-output fiber separations without the danger of photon leakage or "short" by substantially direct pathways.

Different embodiments of system 10 are adapted to perform either a single measurement or a continuous, time-dependent monitoring of the selected physiological property. Visual display for continuous monitoring of the measured values may be added. Furthermore, a warning signal may be issued when the measured value equals to a preselected value.

EXAMPLE

Figure 4:
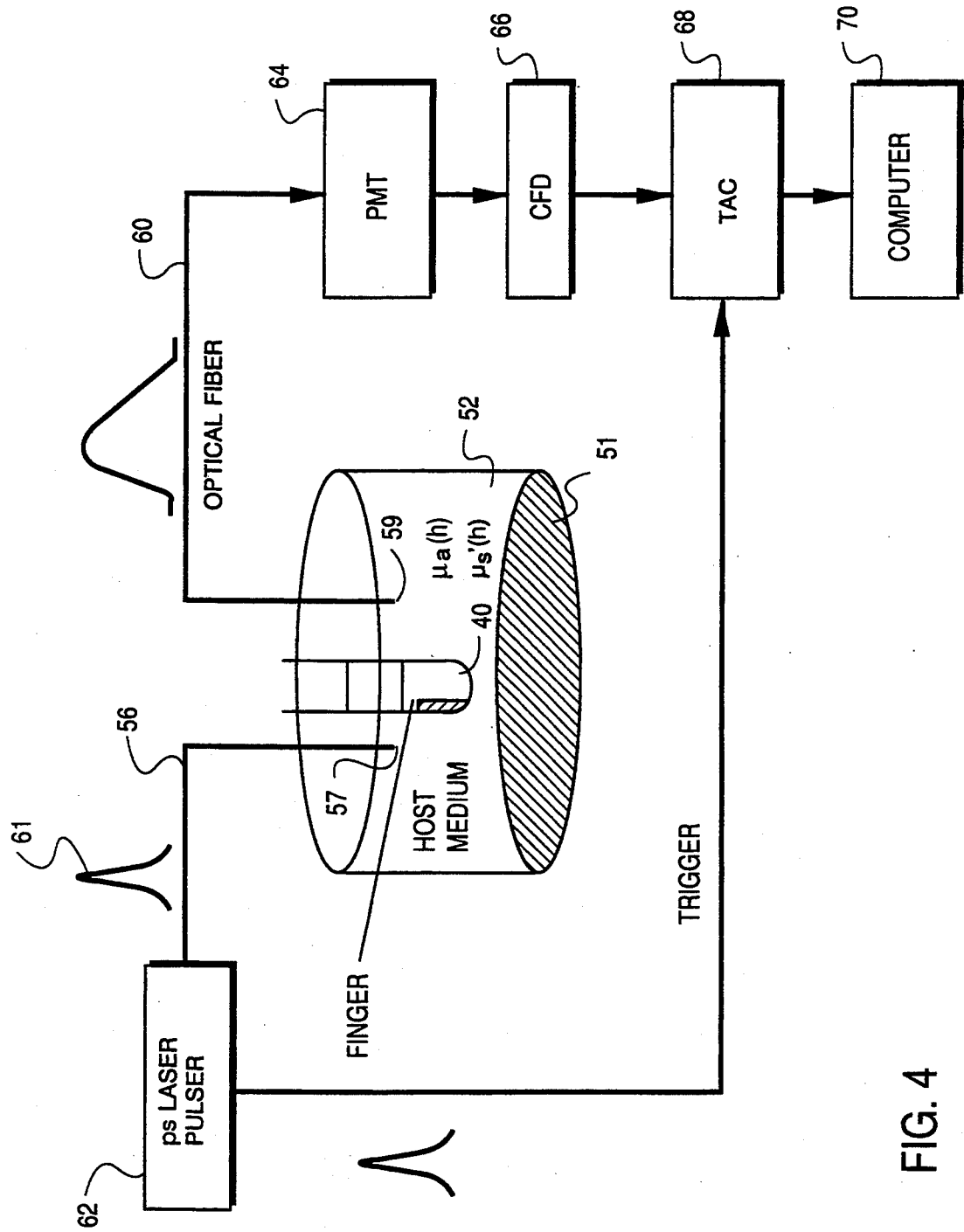
FIG. 4 is a diagrammatic view of a TRS test system used for finger examination.

Referring to FIG. 4, in a test study, a TRS-pulse spectrophotometer was used for quantitative determination of the scattering and absorptive properties of a human finger. To create semi-infinite boundary conditions, examined index finger 40 was immersed into a relatively large volume of intralipid solution 52 with carbon containing india ink. A commercially available intralipid of about 20% concentration was diluted to about 0.5%–2.5% concentration to produce surrounding medium 52. The concentration of the intralipid determines the scattering properties of the solution and the amount of the india ink governs the absorptive properties. Selected amounts of the diluted carbon black ink were added into the matching medium according to the needs. In the test, a 9.4 liter cylinder container 51 of about 15 cm in diameter and 8 cm in height was used to hold matching medium 52. Almost all of the measurements were performed on the index finger of twenty five healthy volunteers (male and female) that included Caucasian, Asian, and African-American population. Fiber ends 57 and 59 of optical fibers 56 and 60 inserted into the host medium several millimeters below the solution surface and maintained in a separation of 3 cm on both sides of examined finger 40. Finger 40 was immersed about 5–6 cm below the surface of surrounding medium 52 in a manner to be located in optical field 54 defined by the immersed ends 57 and 59. This prevented most photons from being transmitted to the surface.

The dual wavelength TRS system with a 5 MHz repetition rate injected 100-ps pulses (61) of red (670 nm) or near-infrared (750 and 830 nm) light created in pulser 62 into medium 52. Optical input fiber 56 of a 1 mm diameter and optical output fiber 60 of a 2 mm diameter were used. The detector consisted of a microchannel-plate photomultiplier tube 64 (MCP-PMT) with a time resolution of 150 ps connected to a constant fraction discriminator (CFD) 66. The single photon counting system included a time amplitude converter (TAC) 68 and computer 70 for registering digitized data. The TRS measurements were taken both in the absence and in the presence of finger 40.

The above-described matching method was used by first increasing the absorption coefficient $\mu_a(h)$ of surrounding medium 52 by adding the diluted black ink. Once the appropriate absorber concentration was determined, the second titration process was used to determine $\mu_s'(h)$ by increasing the concentration of the intralipid.

The TRS data were deconvoluted with the instrumental function that compensates for the instrument's response. The values of $\mu_a$, $\mu_s'$, and $T_o$ (i.e., the laser pulse injection time) were least-square fitted. The absorption coefficient $\mu_a$ and the scattering coefficient $\mu_s'$ were expressed using $\log_{10}$ base, which can be converted to $\log_e$ base simply by multiplying 2.303. (NOTE: for $\mu_s$ calculated by Eq. 9 this conversion cannot be used.)

Figure 4A:
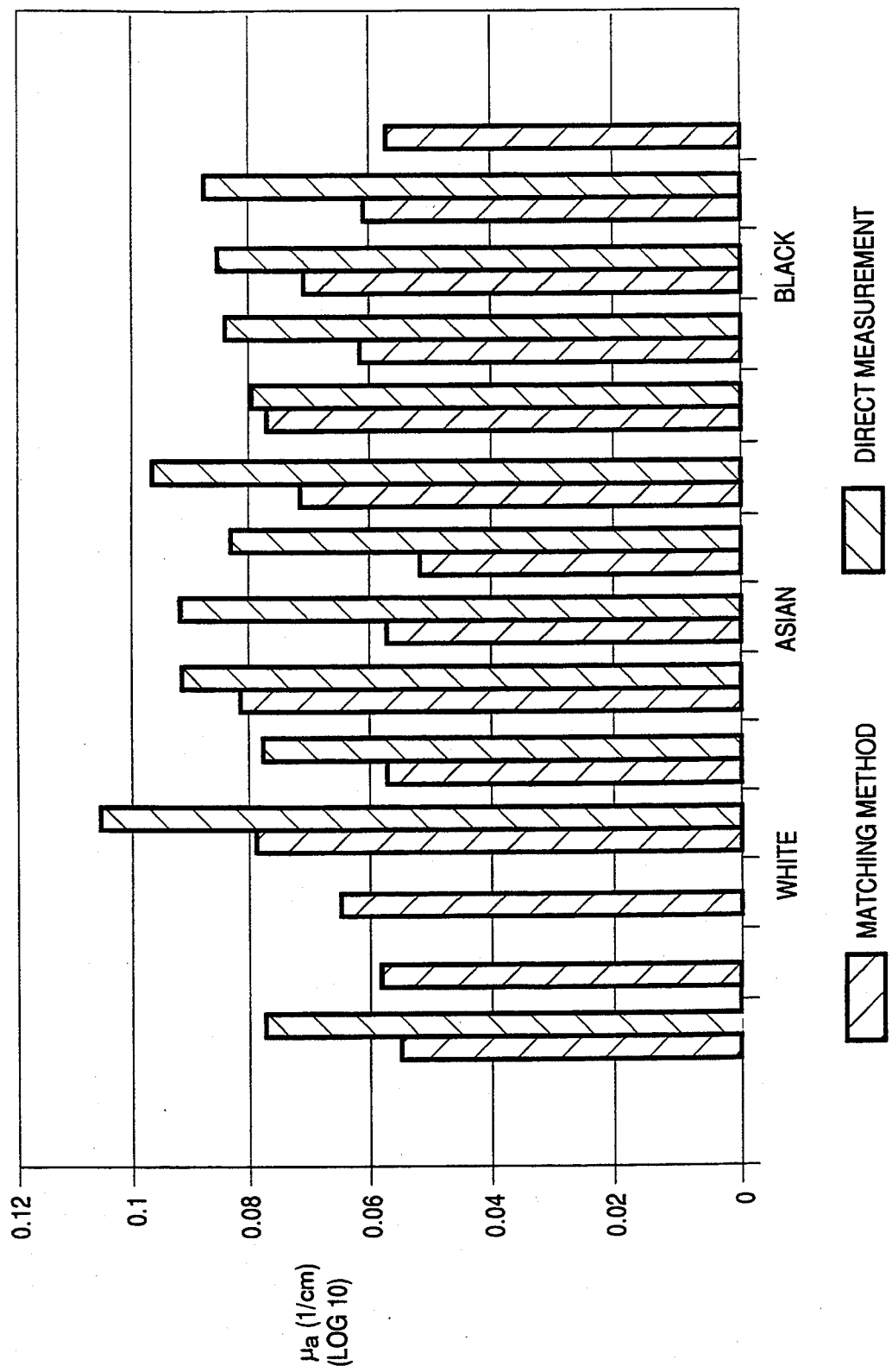
FIGS. 4A and 4B display measured values of the absorption coefficient measured in a test, and FIG. 4C displays their relative occurrence.
Figure 4B:
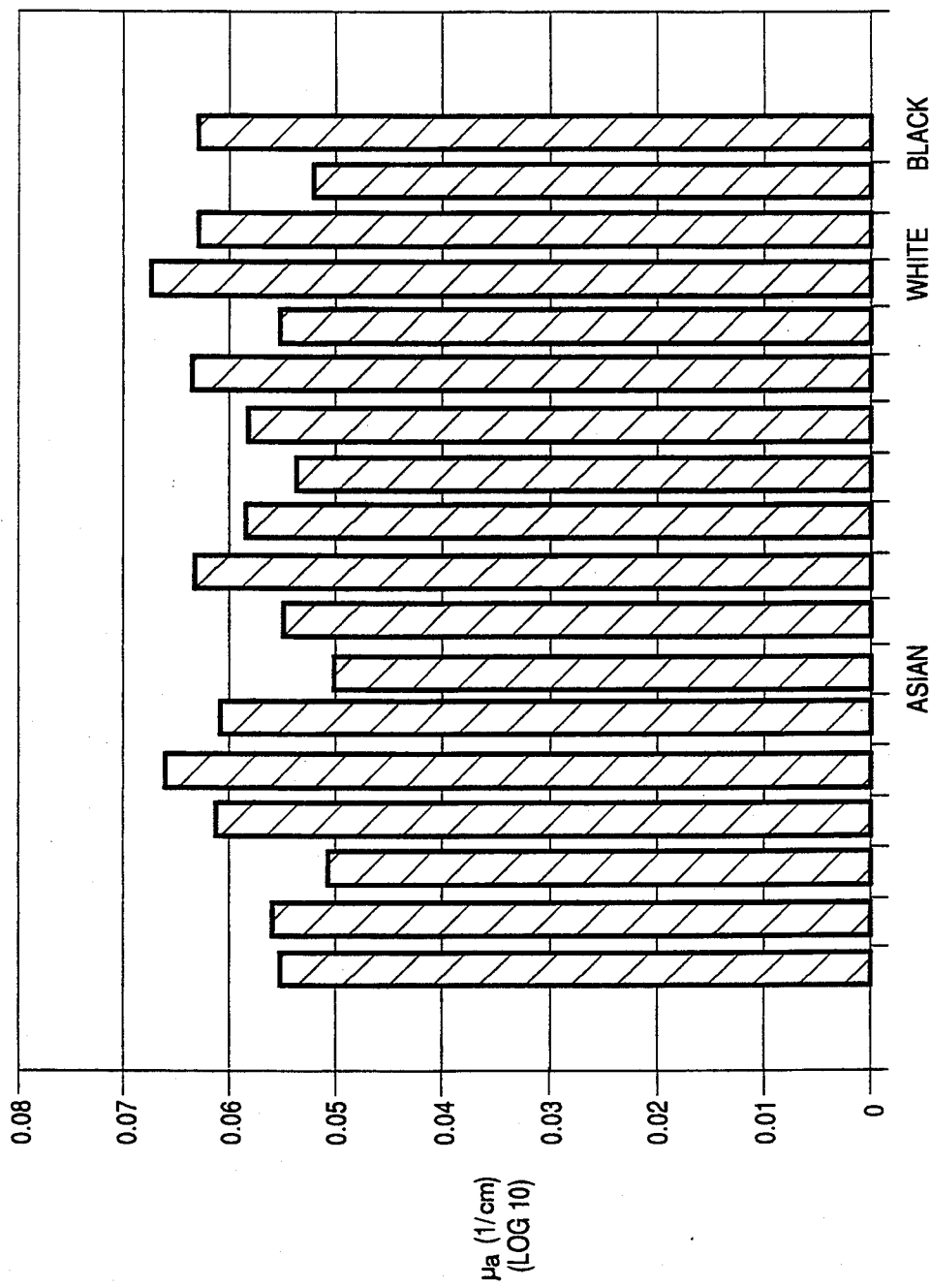
Figure 4C:
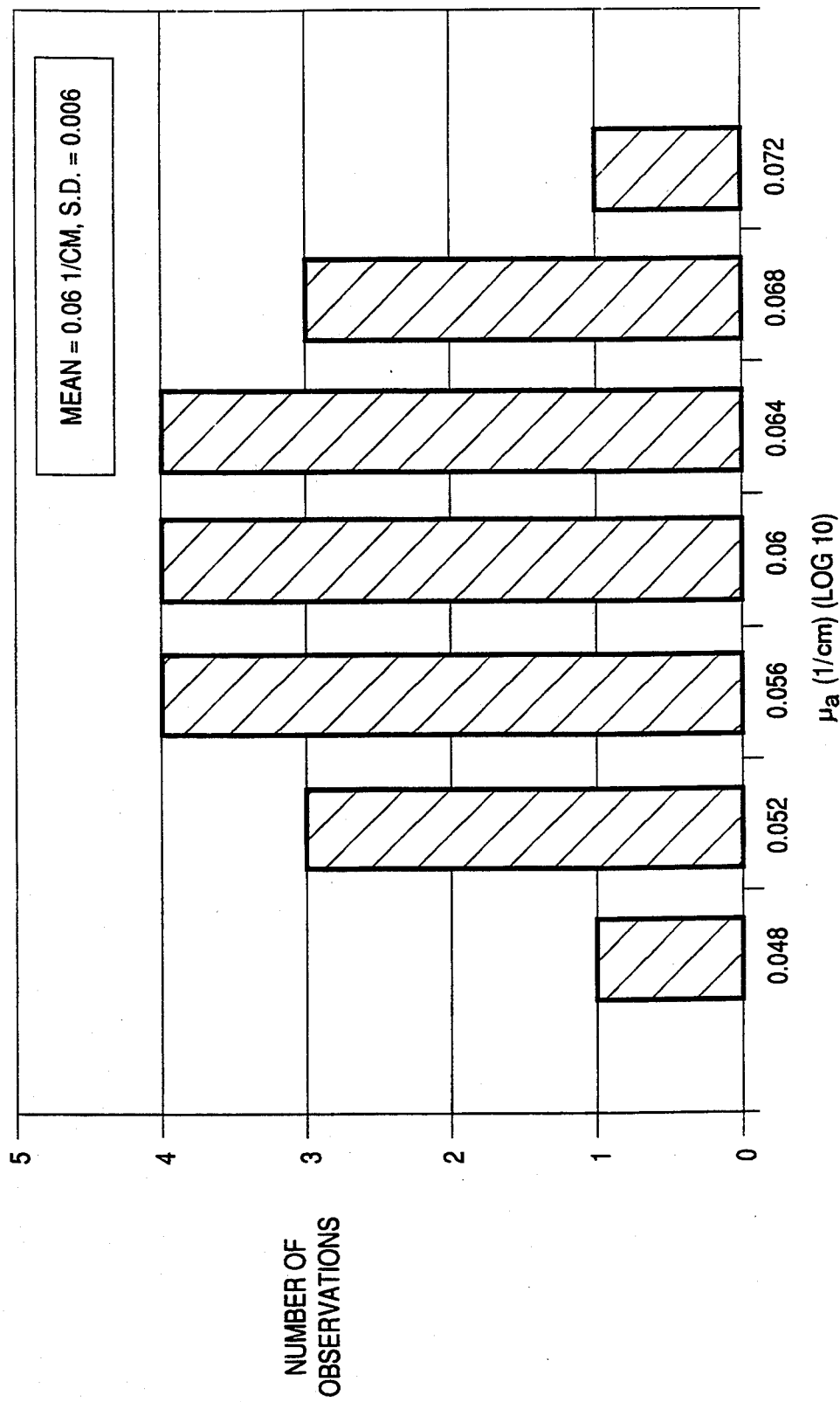
FIGS. 4D and 4E display measured values of the scattering coefficient and their relative occurrence respectively.
FIGS. 4F and 4G display calculated values of the hemoglobin saturation and their relative occurrence, respectively.

FIG. 4A displays the absorption coefficients obtained on fourteen people, (four Caucasian, five Asians, and five African-American) with the matching method and direct measurement, respectively, at 670 nm wavelength and a 2.5 cm interfiber distance. The relative values of $\mu_a$ obtained in the matching measurement varied from 0.05 cm$^{-1}$ to 0.08 cm$^{-1}$, apparently randomly among the three populations; however, the values in the direct measurement varied even more. The direct measurement gives much higher values of $\mu_a$ than the values obtained with the matching method which may be due to photon escape from the finger surface when the optical fibers are attached to the measured finger directly. FIG. 4B shows the absorption values measured for a different group of volunteers. FIG. 4C shows the values of $\mu_a$ as a function of the number of observations. In this study, no relationship was found between the finger diameter and the absorption coefficients $\mu_a$ indicating that the size of the finger has no effect on $\mu_a$.

Figure 4E:
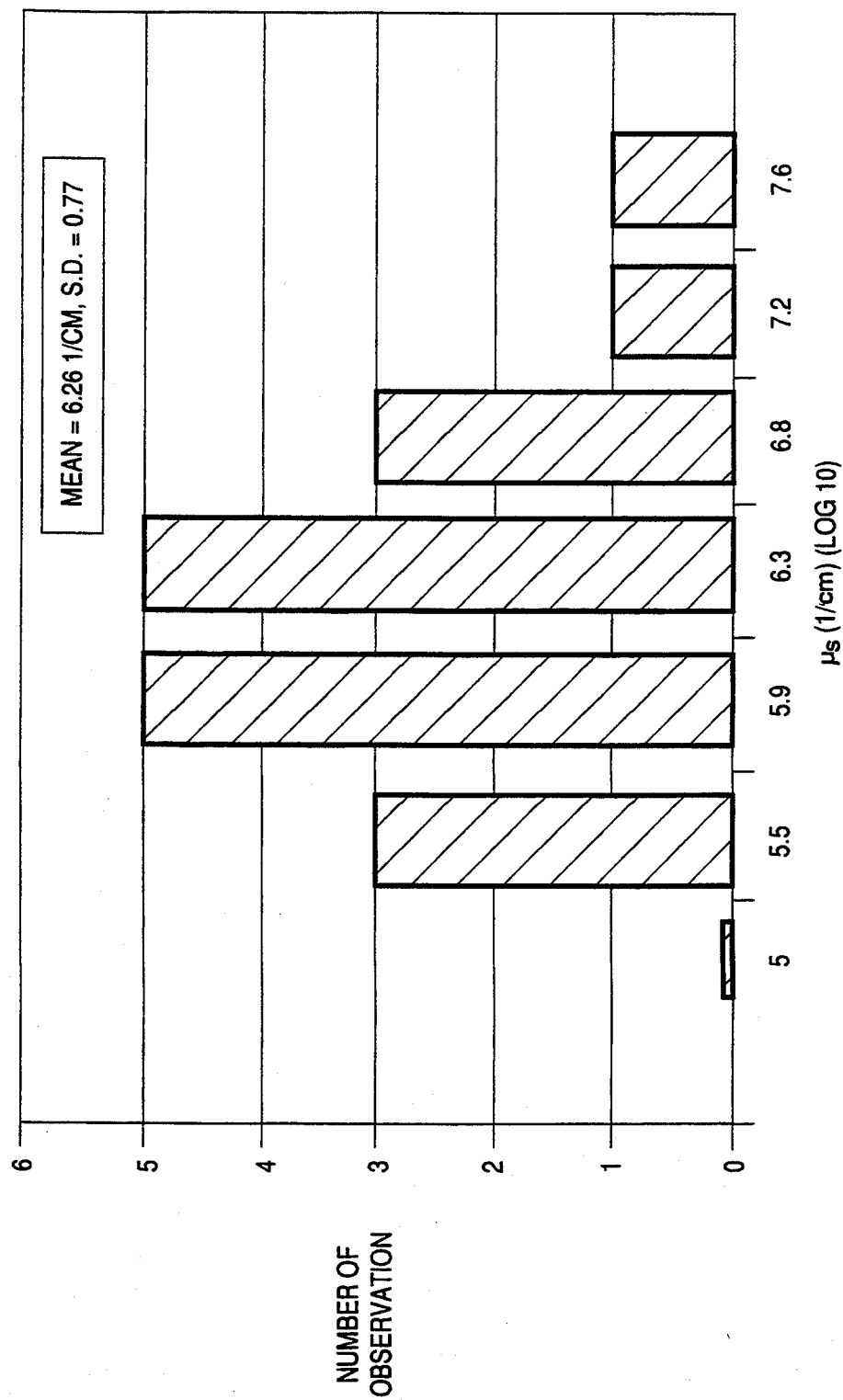

FIG. 4D display $\mu_s$ at measured 670 nm by the matching method for the fourteen individuals of FIG. 4A. The scattering data are summarized in FIG. 4E as a function of the relative occurrence of $\mu_s$. The mean value is 6.26 cm$^{-1}$ and the standard error is 0.64 cm$^{-1}$ with an approximately gaussian distribution.

Figure 4F:
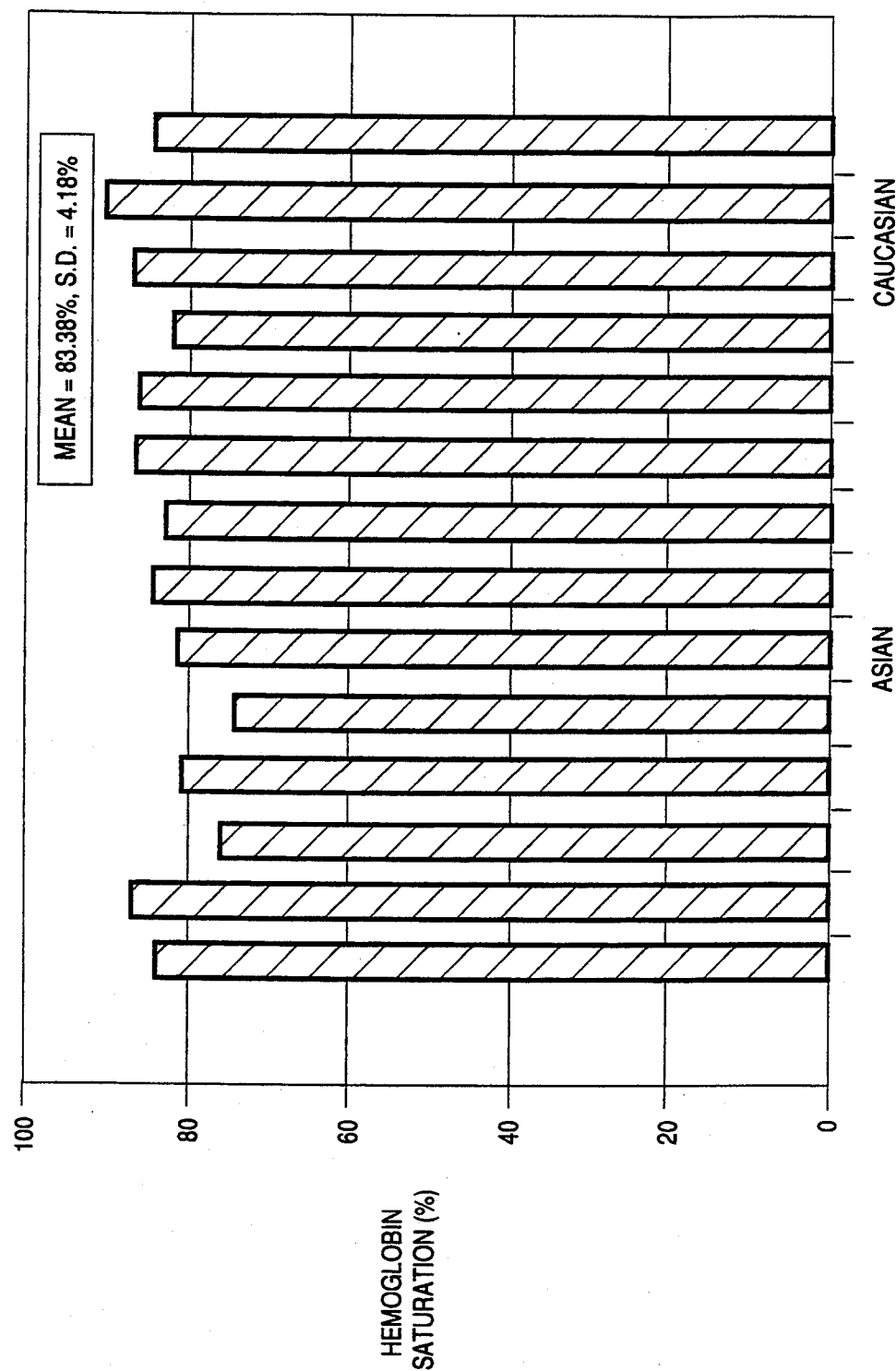
Figure 4G:
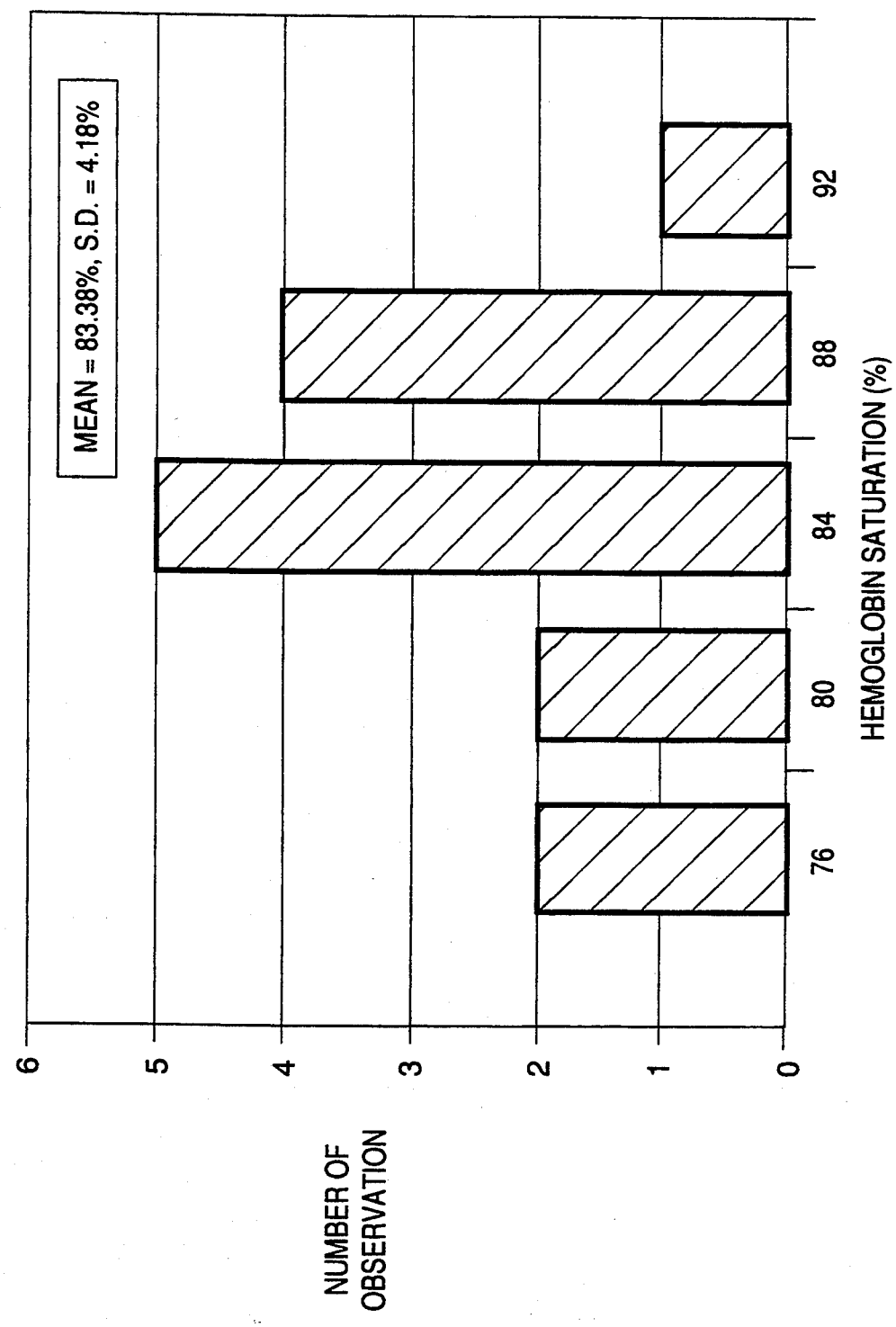

The quantitative hemoglobin saturation of the finger was measured at 670 nm and 750 nm. Since the contribution of water absorption at 750 nm is relatively high, it was necessary to subtract water absorption background from the calculated value of $\mu_a$. For this purpose, we assumed the absorption coefficients of water at 750 nm and 670 nm equal to 0.004 1/cm and 0.026 1/cm, respectively. The background corrected values of $\mu_a$ and the corresponding hemoglobin saturation values are shown in the following table and plotted in FIGS. 4F and 4G.

| Subject | $\mu_a^{670}$ (1/cm) | $\mu_a^{750}$ (1/cm) | $\mu_a^{670}/\mu_a^{750}$ | Y (%) |
|---|---|---|---|---|
| 1 | 0.05119 | 0.04453 | 1.14948 | 83.88 |
| 2 | 0.0467 | 0.04386 | 1.0647 | 87.47 |
| 3 | 0.0578 | 0.04424 | 1.30663 | 76.20 |
| 4 | 0.06276 | 0.05204 | 1.20588 | 81.29 |
| 5 | 0.05743 | 0.04286 | 1.339860 | 74.38 |
| 6 | 0.05045 | 0.04275 | 1.18023 | 82.49 |
| 7 | 0.05936 | 0.05234 | 1.13417 | 84.55 |
| 8 | 0.0493 | 0.04187 | 1.17756 | 82.61 |
| 9 | 0.05488 | 0.0513 | 1.06981 | 87.26 |
| 10 | 0.05012 | 0.0457 | 1.09662 | 86.16 |
| 11 | 0.05992 | 0.04895 | 1.22418 | 80.41 |
| 12 | 0.04848 | 0.04492 | 1.07935 | 86.87 |
| 13 | 0.05206 | 0.05207 | 0.99973 | 90.01 |
| 14 | 0.6463 | 0.05608 | 1.15249 | 83.74 |

Other embodiment are within the following claims:

I claim:

1. A spectrophotometric method of examination of an object of interest using visible or infra-red radiation introduced to a path passing through the object, said method comprising the steps of:
   (a) providing, around said object, optical means for limiting escape of or accounting for escaped photons from inside to outside of said object,
   (b) introducing into the object, at an optical input port, electromagnetic radiation of a selected wavelength in the visible or infra-red range,
   (c) detecting radiation that has migrated in said object from said input port to an optical detection port, and
   (d) determining an optical property of said object based on the changes between the introduced and the detected radiation.

2. The spectrophotometric method of claim 1 wherein said optical means for limiting escape of photons comprise an optical medium at least partially surrounding said object having selectable optical property.

3. The spectrophotometric method of claim 1 wherein said determining step comprises:
   (e) selecting said optical means having a surrounding optical medium with the optical property comparable to the optical property of said object,
   (f) measuring the optical property of said object by performing said (b) and (c) steps,
   (g) selecting another optical means having the optical property of said surrounding medium matched closer to the optical property of said object, and
   (h) repeating iteratively said (f) and (g) steps until the optical property of said surrounding medium is substantially matched to the optical property of said object.

4. A spectrophotometric method of examination of a relatively small volume of biological tissue of interest using visible or infra-red radiation, said method comprising the steps of:
   (a) providing an optical medium of a relatively large volume having selected scattering or absorptive properties, said optical medium adapted to limit escape of or account for escaped photons from inside to outside of said biological tissue of interest,
   (b) introducing said biological tissue of interest into said medium so that it occupies a part of an optical path between an optical input port and an optical detection port and creates a tissue-medium optical path,
   (c) introducing, at said input port located in said medium, electromagnetic radiation of a selected wavelength in the visible or infra-red range,
   (d) detecting, at said detection port located in said medium, radiation that has migrated through said tissue-medium path,
   (e) determining scattering or absorptive properties of said tissue by comparing values of said detected radiation to values of radiation corresponding to said medium of said selected scattering and absorptive properties, and
   (f) examining a physiological property of said tissue based on said determined scattering or absorptive properties of said tissue.

5. A spectrophotometric method of examination of a relatively small volume of biological tissue of interest using visible or infra-red radiation, said method comprising the steps of:
   (a) providing an optical medium of a relatively large volume having selectable scattering or absorptive properties,
   (b) introducing, at an input port located in said medium, electromagnetic radiation of a selected wavelength in the visible or infra-red range,
   (c) detecting, at a detection port located in said medium, radiation that has migrated through a path in said medium from the input port, (d) determining from said detected radiation a scattering or absorptive property of said path, (e) introducing said biological tissue of interest into said medium so that it occupies a part of said path to create a tissue-medium optical path, (f) determining scattering or absorptive properties of said tissue-medium optical path by repeating steps (b), (c) and (d), and (g) examining a physiological property of said tissue based on the differences between the scattering property or the absorptive property of said optical path and said tissue-medium path.

6. A spectrophotometric method of examination of a relatively small volume of biological tissue of interest using visible or infra-red radiation, said method comprising the steps of:

(a) providing an optical medium of a relatively large volume having selected scattering or absorptive properties, (b) introducing said biological tissue of interest into said medium so that it occupies a part of an optical path between an optical input port and an optical detection port to create a tissue-medium optical path, (b) introducing, at said input port located in said medium, pulses having duration on the order of less than a nanosecond of a selected wavelength of visible or infra-red radiation, (c) detecting over time, at said detection port located in said medium, radiation that has migrated through said tissue-medium path, (d) determining a change in the shape of the detected pulse waveform, at said wavelength, relative to the input pulse waveform, (d) determining scattering or absorptive properties of said tissue by comparing said changed waveform to a waveform corresponding to said medium of said selected scattering and absorptive properties, and (e) examining a physiological property of said tissue based on said determined scattering or absorptive properties.

7. A spectrophotometric method of examination of a relatively small volume of biological tissue of interest using visible or infra-red radiation, said method comprising the steps of:

(a) providing an optical medium of a relatively large volume having selected scattering or absorptive properties, (b) introducing said biological tissue of interest into said medium so that it occupies a part of an optical path between an optical input port and an optical detection port to create a tissue-medium optical path, (b) introducing, at said input port located in said medium, an electromagnetic signal of a selected wavelength in the visible or infra-red range, said signal having been modulated by a carrier waveform of frequency that enables determination of an average length of said optical path, (c) detecting, at said detection port located in said medium, radiation that has migrated through said tissue-medium path, (d) comparing the detected signal with the introduced signal and determining therefrom the phase shift of said detected signal from said introduced signal, said phase shift being indicative of said scattering and absorptive properties of said tissue-medium path, (e) determining scattering or absorptive properties of said tissue based on said detected phase shift and the phase shift corresponding to said medium of said selected scattering and absorptive properties, and (e) examining a physiological property of said tissue based on said determined scattering or absorptive properties.

8. The method of claim 4, 5, 6 or 7 further comprising the steps of introducing known changes in the scattering property or the absorptive property of said medium until the scattering or absorptive property measured for said tissue-medium path matches the respective property of said medium.

9. The method of claim 8 further comprising the step of employing the known value of said changes in determining said physiological property.

10. The method of claim 4, 5, 6 or 7 wherein said physiological property is hemoglobin saturation.

11. The method of claim 4, 5, 6 or 7 wherein said tissue is a human finger.

12. The method of claim 4, 5, 6 or 7 wherein said tissue is a biopsy specimen.

13. A spectrophotometric system for examination of an object of interest using visible or infra-red radiation introduced to a path passing through the object, said system comprising:

a spectrophotometer including an optical input port adapted to introduce radiation into the object and an optical detection port adapted to detect radiation that has migrated through a path in the object, photon escape preventing means arranged around the object of interest and adapted to limit escape of or account for escaped photons from inside to outside of the object, processing means adapted to determine an optical property of the object based on the changes between the introduced and the detected radiation.

14. The spectrophotometric system of claim 13 wherein said photon escape preventing means comprise an optical medium at least partially surrounding said object and having a selectable optical property.

15. A system for examination of a relatively small volume of biological tissue of interest using visible or infra-red radiation comprising:

a spectrophotometer including
a light source adapted to introduce radiation at an optical input port,
a detector adapted to detect radiation that has migrated through a path from said input port to an optical detection port,
a processor adapted to evaluate changes between the introduced and the detected radiation, an optical medium of a relatively large volume having selectable scattering properties or absorptive properties, positioning means adapted to locate said biological tissue of interest into said migration path to create a tissue-medium optical path, said optical medium substantially limiting escape of or accounting for escaped photons from inside of said tissue, and said processor further adapted to determine a physiological property of said tissue based on the detected optical property of said tissue-medium optical path and said scattering or absorptive properties of said optical medium.

16. A system for examination of a relatively small volume of biological tissue of interest using visible or infra-red radiation comprising:

a phase modulation spectroscopy unit including a light source adapted to introduce, at an input port, an electromagnetic signal of a selected wavelength in the visible or infra-red range, said signal having been modulated by a carrier waveform of frequency of the order of $10^8$ Hz, a detector adapted detect, at a detection port, radiation that has migrated through on a path from said input port, a phase detector adapted to compare the detected signal with the introduced signal and to determine therefrom the phase shift of said detected signal from said introduced signal, an optical medium of a relatively large volume having selectable scattering properties or absorptive properties, positioning means adapted to locate said biological tissue of interest into said migration path to create a tissue-medium optical path, said optical medium substantially limiting escape of or accounting for escaped photons from inside of said tissue, and processor adapted to determine a physiological property of said tissue based on the detected phase shift and the phase shift corresponding to said optical medium of said selected scattering or absorptive properties.

17. A system for examination of a relatively small volume of biological tissue of interest using visible or infra-red radiation comprising:

a time resolved spectroscopy unit including a light source adapted to introduce at said input port pulses, having duration on the order of less than a nanosecond, of a selected wavelength of visible or infra-red radiation, a detector adapted to detect, over time, at a detection port, radiation that has migrated through a path is said tissue, a processor adapted to determine a change in the shape of the detected pulse waveform, at said wavelength, relative to the introduced pulse waveform, an optical medium of a relatively large volume having selectable scattering properties or absorptive properties, positioning means adapted to locate said biological tissue of interest into the migration path to create a tissue-medium optical path, said optical medium substantially limiting escape of or accounting for escaped photons from inside of said tissue, and said processor further adapted to determine a physiological property of said tissue by comparing said changed waveform to a waveform corresponding to said optical medium having said selected scattering or absorptive properties.

18. The system of claim 15, 16 or 17 or further comprising another optical medium with different scattering or absorptive properties selected correspond to the respective property of said tissue.

19. The system of claim 15, 16 or 17 or wherein said physiological property is hemoglobin saturation.

20. The system of claim 15, 16 or 17 wherein said tissue is a human finger.

21. The system of claim 15, 16 or 17 wherein said tissue is a biopsy specimen.

22. A spectrophotometric method of examination of an object of interest using visible or infra-red radiation introduced to a path passing through the object, said method comprising the steps of:

(a) providing, around said object, optical medium adapted to limit escape of or account for escaped photons from inside to outside of the object, (b) introducing into the object, at an optical input port, electromagnetic radiation of a selected wavelength in the visible or infra-red range, (c) detecting radiation that has migrated in said object from said input port to an optical detection port, and (d) determining an optical property of said object based on the changes between the introduced and the detected radiation.

23. The spectrophotometric method of claim 22 wherein said optical medium has a selectable optical property.

24. The spectrophotometric method of claim 2 or 23 wherein said selectable optical property is an absorption coefficient or a scattering coefficient.

25. The spectrophotometric method of claim 24 wherein said optical property is substantially matched to an optical property of said object.

26. The spectrophotometric method of claim 22 wherein said determining step comprises:

(e) selecting said optical medium with the optical property comparable to the optical property of said object, (f) measuring the optical property of said object by performing said (b) and (c) steps, (g) selecting another optical medium matched closer to the optical property of said object, and (h) repeating iteratively said (f) and (g) steps until the optical property of said medium is substantially matched to the optical property of said object.

27. A spectrophotometric system for examination of an object of interest using visible or infra-red radiation introduced to a path passing through the object, said system comprising:

a spectrophotometer including an optical input port, adapted to introduce radiation into the object, and an optical detection port, adapted to detect radiation that has migrated through a path in the object, a photon escape medium arranged around the object of interest and adapted to limit escape of or account for escaped photons from inside to outside of the object, a processor, connected to said spectrophotometer, adapted to determine an optical property of the object based on the changes between the introduced and the detected radiation.

28. The spectrophotometric system of claim 13 or 27 wherein said spectrophotometer is a continuous wave spectrophotometer.

29. The spectrophotometric system of claim 13 or 27 wherein said spectrophotometer is a phase modulation spectrophotometer.

30. The spectrophotometric system of claim 13 or 27 wherein said spectrophotometer is a time resolved spectrophotometer.

31. The spectrophotometric system of claim 27 wherein said photon escape medium comprises an optical medium at least partially surrounding said object and having a selectable optical property.

32. The spectrophotometric method of claim 14 or 31 wherein said selectable optical property is an absorption coefficient or a scattering coefficient.

33. The spectrophotometric system of claim 32 wherein said optical property is substantially matched to an optical property of said object.

* * * * *